US006815188B2

(12) United States Patent
Friddle et al.

(10) Patent No.: US 6,815,188 B2
(45) Date of Patent: Nov. 9, 2004

(54) HUMAN KINASES AND POLYNUCLEOTIDES ENCODING THE SAME

(75) Inventors: Carl Johan Friddle, The Woodlands, TX (US); Erin Hilbun, Houston, TX (US); Brian Mathur, The Woodlands, TX (US); C. Alexander Turner, Jr., The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 10/434,034

(22) Filed: May 8, 2003

(65) Prior Publication Data

US 2003/0181705 A1 Sep. 25, 2003

Related U.S. Application Data

(63) Continuation of application No. 09/992,481, filed on Nov. 19, 2001, now Pat. No. 6,593,125.
(60) Provisional application No. 60/252,011, filed on Nov. 20, 2000.

(51) Int. Cl.[7] .......................... C12N 9/12; C12N 15/00; C12N 5/00; C12N 1/20; C07K 1/00
(52) U.S. Cl. ..................... 435/194; 530/350; 435/252.3; 435/320.1; 435/325; 435/6
(58) Field of Search .............................. 435/194, 252.3, 435/320.1, 325; 530/350

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,873,191 A | 10/1989 | Wagner et al. |
| 4,946,778 A | 8/1990 | Ladner et al. |
| 5,252,743 A | 10/1993 | Barrett et al. |
| 5,272,057 A | 12/1993 | Smulson et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,700,637 A | 12/1997 | Southern |
| 5,723,323 A | 3/1998 | Kauffman et al. |
| 5,744,305 A | 4/1998 | Fodor et al. |
| 5,830,721 A | 11/1998 | Stemmer et al. |
| 5,837,458 A | 11/1998 | Minshull et al. |
| 5,869,336 A | 2/1999 | Meyer et al. |
| 5,877,397 A | 3/1999 | Lonberg et al. |
| 5,948,767 A | 9/1999 | Scheule et al. |
| 6,034,228 A | 3/2000 | Norris et al. |
| 6,075,181 A | 6/2000 | Kucherlapati et al. |
| 6,110,490 A | 8/2000 | Thierry |
| 6,117,679 A | 9/2000 | Stemmer |
| 6,150,584 A | 11/2000 | Kucherlapati et al. |

OTHER PUBLICATIONS

Database EMBL 'Online! Aug. 18, 1998, National Cancer Institute, Cancer Genome Anatomy Project: Data Accession No. A1086865, XP002196922, oz86d02.x1, Soares senescent fibroblasts NbHSF, *Homo sapiens* cDNA clone Image: 1682211 3 similar to WP: ZC581.1 CE15235 SER/THR–Protein Kinase.
Database EMBL 'Online! Apr. 18, 1997, Adams MD et al.: Database accession No. HSZZ88419, XP002196923, EST96652 Testis I *Homo sapiens* cDNA 5' end similar to SER/THR kinase p78.
International Search Report.
Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbera–Garapin et al, 1981, "A New Dominant Hybrid Selective Marker for Higher Eukaryotic Cells", J. Mol. Biol. 150:1–14.
Gautier et al, 1987, "αDNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.
Gordon, 1989, "Transgenic Animals", International Review of Cytology, 115:171–229.
Greenspan et al, 1993, "Idiotypes: structure and immunogenicity", FASEB Journal 7:437–444.
Gu et al, 1994, "Deletion of a DNA Polymerase β Gene Segment in T Cells Using Cell Type–Specific Gene Targeting", Science 265:103–106.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985, "Up–promoter mutations in the lpp gene of *Escherichia coli*", Nucleic Acids Research 13(9):3101–3110.
Janknecht et al, "Rapid and efficient purification of native histidine–tagged protein expressed by recombinant vaccinia virus", PNAS 88:8972–8976.

(List continued on next page.)

Primary Examiner—Maryam Monshipouri

(57) ABSTRACT

Novel human polynucleotide and polypeptide sequences are disclosed that can be used in therapeutic, diagnostic, and pharmacogenomic applications.

5 Claims, No Drawings

OTHER PUBLICATIONS

Kohler & Milstein, 1975, "Continuous cultures of fused cells secreting antibody of predefined specificity", Nature 256:495–497.

Lakso et al, 1992, "Targeted oncogene activation by site–specific recombination in transgenic mice", Proc. Natl. Acad. Sci. USA 89:6232–6236.

Lavitrano et al, 1989, "Sperm Cells as Vectors for introducing Foreign DNA into Eggs: Genetic Transformation of Mice", Cell 57:717–723.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984 "Recombinant antibodies possessing novel effector functions", Nature 312:604–608.

Nisonoff, 1991, "Idiotypes: Concepts and Applications", J. of Immunology 147:2429–2438.

O'Hare et al, "Transformation of mouse fibroblasts to methotrexate resistance by a combinant plasmid expressing a prokaryotic dihydrofolate reductase", Proc. Natl. Acad. Sci. USA 78(3):1527–1531.

Santerre et al, 1984, "Expression of prokaryotic genes for hygromycin B and G418 resistance as dominant–selection markers in mouse L cells", Gene 30:147–156.

Stein et al, 1988, "Physiochemical properties of phosphorothioate oligodeoxynucleotides", Nucleic Acids Research 16(8):3209–3221.

Van Der Putten et al, 1985, "Efficient insertion of genes into the mouse germ line via retroviral vectors", Proc. Natl. Acad. Sci. USA 82:6148–6152.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

HUMAN KINASES AND POLYNUCLEOTIDES ENCODING THE SAME

The present application is a continuation of U.S. patent application Ser. No. 09/992,481, filed Nov. 19, 2001, now U.S. Pat. No. 6,593,125 issued Jul. 15, 2003, which claims the benefit of U.S. Provisional Application No. 60/252,011, which was filed on Nov. 20, 2000, each of which are herein incorporated by reference in their entirety.

1. INTRODUCTION

The present invention relates to the discovery, identification, and characterization of novel human polynucleotides encoding proteins sharing sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over-express the disclosed genes, antagonists and agonists of the proteins, and other compounds that modulate the expression or activity of the proteins encoded by the disclosed genes, which can be used for diagnosis, drug screening, clinical trial monitoring, the treatment of diseases and disorders, and cosmetic or nutriceutical applications.

2. BACKGROUND OF THE INVENTION

Kinases mediate the phosphorylation of a wide variety of proteins and compounds in the cell. In conjunction with phosphatases, kinases are involved in a range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins and the corresponding amino acid sequences of these proteins. The novel human proteins (NHPs) described for the first time herein share structural similarity with animal kinases, including, but not limited to, receptor tyrosine kinases (SEQ ID NOS:1–2 show particular similarity to NEK family kinases, and SEQ ID NOS:3–5 are particularly similar to calcium and calmodulin dependent kinases as well as sequences encoding PK 80), and serine-threonine kinases. The described NHPs encode novel kinases having homologues and orthologs across a range of phyla and species.

The novel human polynucleotides described herein encode open reading frames (ORFs) encoding proteins of 692 and 817 amino acids in length (see respectively SEQ ID NOS:2 and 4).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–5 are "knocked-out" they provide a method of identifying phenotypic expression of the particular gene as well as a method of assigning function to previously unknown genes. In addition, animals in which the unique NHP sequences described in SEQ ID NOS:1–5 are "knocked-out" provide a unique source in which to elicit antibodies to homologous and orthologous proteins that would have been previously viewed by the immune system as "self" and therefore would have failed to elicit significant antibody responses. To these ends, gene trapped knockout ES cells have been generated in murine homologs of the described NHPs.

Additionally, the unique NHP sequences described in SEQ ID NOS:1–5 are useful for the identification of protein coding sequence and mapping a unique gene to a particular chromosome (the gene encoding SEQ ID NOS:1–2 is apparently encoded on human chromosome 17, see GENBANK accession no. AC010761, and the gene encoding SEQ ID NOS:3–5 is apparently encoded on human chromosome 3, see GENBANK accession no. AC068979). These sequences identify biologically verified exon splice junctions as opposed to splice junctions that may have been bioinformatically predicted from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NHP expression and/or NHP activity that utilize purified preparations of the described NHPs and/or NHP products, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human kinase proteins. SEQ ID NO:5 describes a NHP ORF and flanking sequences.

5. DETAILED DESCRIPTION OF THE INVENTION

The NHPs described for the first time herein are novel proteins that are expressed in, inter alia, human cell lines and pituitary, thymus, spleen, lymph node, bone marrow, trachea, kidney, prostate, testis, thyroid, adrenal gland, pancreas, salivary gland, stomach, small intestine, skeletal muscle, heart, uterus, placenta, adipose, skin, bladder, rectum, pericardium, ovary, fetal kidney, fetal lung, gall bladder, tongue, aorta, 6-, 9-, and 12-week embryos, adenocarcinoma, osteosarcoma, and embryonic carcinoma cells (SEQ ID NOS:1–2). SEQ ID NOS:3–5 were predominantly expressed in fetal brain, brain, spinal cord, thymus, lymph node, trachea, lung, prostate, testis, thyroid, adrenal gland, stomach, small intestine, skeletal muscle, uterus, placenta, mammary gland, skin, bladder, pericardium, hypothalamus, fetal kidney, fetal lung, tongue, aorta, 6-, 9-, and 12-week embryos, and embryonic carcinoma cells.

The described sequences were compiled from sequences available in GENBANK, and cDNAs generated from pituitary, lymph node, mammary gland, brain, adrenal gland, fetus, and testis mRNAs (Edge Biosystems, Gaithersburg, Md.).

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of an NHP that correspond to functional domains, and the polypeptide products specified by such nucleotide sequences, including, but not limited to, the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including, but not limited to, soluble proteins and peptides in which all or a portion of the signal sequence is deleted; (d) nucleotides that encode chimeric fusion proteins containing all or a portion of a coding region of a NHP, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes the human DNA sequences presented in the Sequence Listing (and vectors comprising the same), and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & Sons, Inc., New York, at p. 2.10.3) and encodes a functionally equivalent expression product. Additionally, contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, and/or directed evolution, as described in, for example, U.S. Pat. Nos. 5,837,458 or 5,723,323, both of which are herein incorporated by reference). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of a NHP (as measured by BLAST sequence comparison analysis using, for example, the GCG sequence analysis package, as described herein, using default parameters).

The invention also includes nucleic acid molecules, preferably DNA molecules, that hybridize to, and are therefore the complements of, the described NHP encoding polynucleotides. Such hybridization conditions can be highly stringent or less highly stringent, as described herein. In instances where the nucleic acid molecules are deoxyoligonucleotides ("DNA oligos"), such molecules are generally about 16 to about 100 bases long, or about 20 to about 80 bases long, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a microarray or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS:1–5 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS:1–5, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445, 934, 5,252,743, 4,713,326, 5,424,186, and 4,689,405, the disclosures of which are herein incorporated by reference in their entirety.

Addressable arrays comprising sequences first disclosed in SEQ ID NOS:1–5 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–5.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–5 provides detailed information about transcriptional changes involved in a specific pathway, potentially leading to the identification of novel components or gene functions that manifest themselves as novel phenotypes.

Probes consisting of sequences first disclosed in SEQ ID NOS:1–5 can also be used in the identification, selection and validation of novel molecular targets for drug discovery. The use of these unique sequences permits the direct confirmation of drug targets and recognition of drug dependent changes in gene expression that are modulated through pathways distinct from the intended target of the drug. These unique sequences therefore also have utility in defining and monitoring both drug action and toxicity.

As an example of utility, the sequences first disclosed in SEQ ID NOS:1–5 can be utilized in microarrays or other assay formats, to screen collections of genetic material from patients who have a particular medical condition. These investigations can also be carried out using the sequences first disclosed in SEQ ID NOS:1–5 in silico and by comparing previously collected genetic databases and the disclosed sequences using computer software known to those in the art.

Thus the sequences first disclosed in SEQ ID NOS:1–5 can be used to identify mutations associated with a particular disease and also in diagnostic and/or prognostic assays.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS:1–5. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), or 60° C. (for 23-base oligos). These nucleic acid molecules may encode or act as NHP gene antisense molecules, useful, for example, in NHP gene regulation (and/or as antisense primers in amplification reactions of NHP gene nucleic acid sequences). With respect to NHP gene regulation, such techniques can be used to regulate biological functions. Further, such sequences can be used as part of ribozyme and/or triple helix sequences that are also useful for NHP gene regulation.

Inhibitory antisense or double stranded oligonucleotides can additionally comprise at least one modified base moiety that is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including, but not limited to, arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized (Stein et al., 1988, Nucl. Acids Res. 16:3209), and methylphosphonate oligonucleotides can be prepared by use of controlled pore glass polymer supports (Sarin et al., 1988, Proc. Natl. Acad. Sci. USA 85:7448–7451), etc.

Low stringency conditions are well-known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Spring Harbor Press, N.Y.; and Ausubel et al., 1989, supra.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individuals genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue known to express or suspected of expressing an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known to express, or suspected of expressing, a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known to express, or suspected of expressing, a mutant NHP allele, in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of carrying, or known to carry, a mutant NHP allele (e.g., a person manifesting a NHP-associated phenotype such as, for example, immune disorders, obesity, high blood pressure, etc.), or a cDNA library can be constructed using RNA from a tissue known to express, or suspected of expressing, a mutant NHP allele. A normal NHP sequence, or any suitable fragment thereof, can then be labeled and used as a probe to identify the corresponding mutant NHP allele in such libraries. Clones containing mutant NHP sequences can then be purified and subjected to sequence analysis according to methods well-known to those skilled in the art.

Additionally, an expression library can be constructed utilizing cDNA synthesized from, for example, RNA isolated from a tissue known to express, or suspected of expressing, a mutant NHP allele in an individual suspected of carrying, or known to carry, such a mutant allele. In this manner, gene products made by the putatively mutant tissue may be expressed and screened using standard antibody screening techniques in conjunction with antibodies raised against a normal NHP product, as described below (for screening techniques, see, for example, Harlow and Lane, eds., 1988, "Antibodies: A Laboratory Manual", Cold Spring Harbor Press, Cold Spring Harbor).

Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to a NHP are likely to cross-react with a corresponding mutant NHP expression product. Library clones detected via their reaction with such labeled antibodies can be purified and subjected to sequence analysis according to methods well-known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721, 5,837,458, 6,117,679, and 5,723,323, which are herein incorporated by reference in their entirety.

The invention also encompasses: (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include, but are not limited to, the cytomegalovirus (hCMV) immediate early gene, regulatable, viral elements (particularly retroviral LTR promoters), the early or late promoters of SV40 and adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic or nuclear proteins (although processed forms or fragments can be secreted or membrane associated), expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and antiidiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 THE NHP SEQUENCES

The cDNA sequences and corresponding deduced amino acid sequences of the described NHPs are presented in the Sequence Listing.

Expression analysis has provided evidence that the described NHPs can be expressed in a range of human tissues, as described in greater detail herein above. In addition to serine-threonine kinases, the described NHPs also share significant similarity to several additional kinase families, including kinases associated with signal transduction, from a variety of phyla and species. Several polymorphisms were identified in the described NHPs. These include a T/C polymorphism in the sequence region represented by nucleotide position 1170 of SEQ ID NO:1, both of which result in the same amino acid being present at the corresponding amino acid (aa) position of SEQ ID NO:2; a T/C polymorphism in the sequence region represented by nucleotide position 1321 of SEQ ID NO:1, both of which result in the same amino acid being present at the corresponding aa position of SEQ ID NO:2; a C/G polymorphism in the sequence region represented by nucleotide position 94 of SEQ ID NO:3, which can result in either a leu or val being present at corresponding aa position 32 of SEQ ID NO:4; an A/G polymorphism at nucleotide position 112 of SEQ ID NO:3, which can result in either a lys or glu being present at corresponding aa position 38 of SEQ ID NO:4; and an A/T polymorphism at nucleotide position 133 of SEQ ID NO:3, which can result in either a thr or ser being present at corresponding aa position 45 of SEQ ID NO:4. The above polymorphisms can be present either singly, or in any combination or permutation within a given sequence.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458, which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to, pronuclear microinjection (Hoppe and Wagner, 1989, U.S. Pat. No. 4,873,191); retrovirus mediated gene transfer into germ lines (Van der Putten et al., 1985, Proc.

Natl. Acad. Sci. USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals that carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPS AND NHP POLYPEPTIDES

NHPs, NHP polypeptides, NHP peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be used as pharmaceutical reagents useful in the therapeutic treatment of mental, biological, or medical disorders and disease. Given the similarity information and expression data, the described NHPs can be targeted (by drugs, oligos, antibodies, etc.) in order to treat disease, or to therapeutically augment the efficacy of therapeutic agents.

The Sequence Listing discloses the amino acid sequences encoded by the described NHP-encoding polynucleotides. The NHPs display initiator methionines that are present in DNA sequence contexts consistent with eucaryotic translation initiation sites. The NHPs do not display consensus signal sequences, which indicates that they may be cytoplasmic or possibly nuclear proteins, however, the homology data and presence of hydrophobic domains indicates that the NHPs are probably membrane associated, or possibly secreted.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing, is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4–1 at page 109 of "Molecular Cell Biology", 1986, J. Darnell et al., eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences, as judged by any of a number of criteria, including, but not limited to, the ability to bind and modify a NHP substrate, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but that result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well-known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing NHP nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited to, the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye and Inouye, 1985, Nucleic Acids Res. 13:3101–3109; Van Heeke and Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) can be used as a vector to express foreign polynucleotide sequences. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., see Logan and Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, may be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al.; 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the desired modification and processing of the foreign protein expressed. To this end, eukaryotic host cells that possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the NHP product. Such engineered cell lines may be particularly useful in screening and evaluation of compounds that affect the endogenous activity of the NHP product.

A number of selection systems may be used, including, but not limited to, the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

Alternatively, any fusion protein can be readily purified by utilizing an antibody specific for the fusion protein being expressed. For example, an exemplary system allows for the ready purification of non-denatured fusion proteins expressed in human cell lines (Janknecht et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively, targeting of NHP or its nucleic acid sequence might be achieved using liposome or lipid complex based delivery systems. Such technologies are described in "Liposomes: A Practical Approach", New, R.R.C., ed., Oxford University Press, New York, and in U.S. Pat. Nos. 4,594,595, 5,459,127, 5,948,767 and 6,110,490 and their respective disclosures, which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. Provisional Patent Application Ser. Nos. 60/111,701 and 60/056,713, both of which are herein incorporated by reference, for examples of such transducing sequences) to facilitate passage across cellular membranes, and can optionally be engineered to include nuclear localization.

5.3 ANTIBODIES TO NHP PRODUCTS

Antibodies that specifically recognize one or more epitopes of a NHP, or epitopes of conserved variants of a NHP, or peptide fragments of a NHP, are also encompassed by the invention. Such antibodies include, but are not limited to, polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, a NHP peptide (e.g., one corresponding to a functional domain of a NHP), truncated NHP polypeptides (NHP in which one or more domains have been deleted), functional equivalents of the NHP, or mutated variants of the NHP. Such host animals may include, but are not limited to, pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique that provides for the production of antibody molecules by continuous cell lines in culture. These include, but are not limited to, the hybridoma technique (Kohler and Milstein, 1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class, including IgG, IgM, IgE, IgA, and IgD, and any subclass thereof. The hybridoma producing the mAbs of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA, 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures, which are herein incorporated by reference in their entirety. Also encompassed by the present invention is the use of fully humanized monoclonal antibodies, as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: F(ab')₂ fragments, which can be produced by pepsin digestion of the antibody molecule; and Fab fragments, which can be generated by reducing the disulfide bridges of the F(ab')₂ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well-known to those skilled in the art (see, e.g., Greenspan and Bona, 1993, FASEB J. 7:437–444; and Nissinoff, 1991, J. Immunol. 147:2429–2438). For example, antibodies that bind to a NHP domain and competitively inhibit the binding of NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies, or Fab fragments of such anti-idiotypes, can be used in therapeutic regimens involving a NHP mediated pathway.

Additionally given the high degree of relatedness of mammalian NHPs, the presently described knock-out mice (having never seen a NHP, and thus never been tolerized to a NHP) have a unique utility, as they can be advantageously applied to the generation of antibodies against the disclosed mammalian NHPs (i.e., a NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. All cited publications, patents, and patent applications are herein incorporated by reference in their entirety.

What is claimed is:

1. An isolated polypeptide comprising the amino acid sequence of SEQ ID NO:2 or SEQ ID NO:4.

2. A substantially isolated protein having the kinase activity of the protein shown in SEQ ID NO:2, which is encoded by a nucleotide sequence that hybridizes to SEQ ID NO:1 under highly stringent conditions.

3. The substantially isolated protein of claim 2, comprising the amino acid sequence of SEQ ID NO:2.

4. A substantially isolated protein having the kinase activity of the protein shown in SEQ ID NO:4, which is encoded by a nucleotide sequence that hybridizes to SEQ ID NO:3 under highly stringent conditions.

5. The substantially isolated protein of claim 4, comprising the amino acid sequence of SEQ ID NO:4.

* * * * *

SEQUENCE LISTING

<160> NUMBER OF SEQ ID NOS: 5

<210> SEQ ID NO 1
<211> LENGTH: 2079
<212> TYPE: DNA
<213> ORGANISM: homo sapiens

<400> SEQUENCE: 1

| | | | | | | |
|---|---|---|---|---|---|---|
| atggagaagt | acgagcggat | ccgagtggtg | gggagaggtg | ccttcgggat | tgtgcacctg | 60 |
| tgcctgcgaa | aggctgacca | gaagctggtg | atcatcaagc | agattccagt | ggaacagatg | 120 |
| accaaggaag | agcggcaggc | agcccagaat | gagtgccagg | tcctcaagct | gctcaaccac | 180 |
| cccaatgtca | ttgagtacta | cgagaacttc | ctggaagaca | aagcccttat | gatcgccatg | 240 |
| gaatatgcac | caggcggcac | tctggctgag | ttcatccaaa | agcgctgtaa | ttccctgctg | 300 |
| gaggaggaga | ccatcctgca | cttcttcgtg | cagatcctgc | ttgcactgca | tcatgtgcac | 360 |
| acccacctca | tcctgcaccg | agacctcaag | acccagaaca | tcctgcttga | caaacaccgc | 420 |
| atggtcgtca | agatcggtga | tttcggcatc | tccaagatcc | ttagcagcaa | gagcaaggcc | 480 |
| tacacggtgg | tgggtacccc | atgctatatc | tcccctgagc | tgtgtgaggg | caagccctac | 540 |
| aaccagaaga | gtgacatctg | ggccctgggc | tgtgtcctct | acgagctggc | cagcctcaag | 600 |
| agggctttcg | aggctgcgaa | cttgccagca | ctggtgctga | agatcatgag | tggcaccttt | 660 |
| gcacctatct | ctgaccggta | cagccctgag | cttcgccagc | tggtcctgag | tctactcagc | 720 |
| ctggagcctg | cccagcggcc | accactcagc | cacatcatgg | cacagcccct | ctgcatccgt | 780 |
| gccctcctca | acctccacac | cgacgtgggc | agtgtccgca | tgcggagggc | agagaagtcc | 840 |
| gtggccccca | gcaacacagg | gagcaggacc | accagtgtcc | gctgcagagg | tatccccgg | 900 |
| ggacctgtga | ggccagccat | cccaccacca | ctgtcgtcag | tgtatgcctg | gggtggtggg | 960 |
| ctgggcaccc | ccctgcggct | gccaatgctc | aacacagagg | tggtccaggt | ggcagctggg | 1020 |

-continued

```
cgcacgcaga aagccggcgt cacgcgctct gggcgtctca tcctgtggga ggccccaccc    1080
ctaggtgcag gcggaggcag tctccttcct ggggcagtgg agcagccaca gccccagttc    1140
atctcgcgtt tcctggaggg ccagtcgggy gtgaccatca agcacgtggc ctgtggggac    1200
ttcttcactg cctgcctgac tgacagaggc atcatcatga cattcggcag cggcagcaat    1260
gggtgcctag gccatggcag cctcactgac atcagccagc ccaccattgt ggaggctttg    1320
ytgggctatg aaatggtgca ggtggcctgt ggggcctctc acgtgctggc cctgtccact    1380
gagcgagaac tatttgcctg gggccgtgga cagcggca gactgggct aggcaccagg       1440
gagtcccaca gctgccccca gcaggtgccc atgcccccag gacaggaagc tcagcgagtt    1500
gtatgtggta tcgattcctc catgatcctc actgtgcctg ccaagccct agcctgtggg     1560
agcaacaggt tcaacaagct gggcctggac cacctctccc tgggggagga gcctgtcccc   1620
caccagcaag tggaggaggc cctgagcttc acactactag gctctgcacc cctggaccag    1680
gagcctctgc tgagtataga cctgggcact gctcactcag ctgctgtgac tgcctcgggt    1740
gattgctaca cttttggcag caatcagcac ggacagttgg gcaccaatac tcgccgaggc    1800
agtcgggcac cctgtaaggt ccaaggcctt gagggcatca agatggcaat ggtagcctgt    1860
ggggatgcct tcactgtagc tattggggca gagagcgaag tgtactcttg gggcaaaggg    1920
gcgcgaggtc gattgggaag gagggatgag gatgccggac tccctcggcc agtgcagttg    1980
gatgagacac cccttacac ggtgacttcc gtgtcctgtt gccatggaaa cacctcctg     2040
gctgttcgat cggtcacaga tgagccggtc ccccctga                            2079
```

<210> SEQ ID NO 2
<211> LENGTH: 692
<212> TYPE: PRT
<213> ORGANISM: homo sapiens

<400> SEQUENCE: 2

```
Met Glu Lys Tyr Glu Arg Ile Arg Val Val Gly Arg Gly Ala Phe Gly
  1               5                  10                  15

Ile Val His Leu Cys Leu Arg Lys Ala Asp Gln Lys Leu Val Ile Ile
             20                  25                  30

Lys Gln Ile Pro Val Glu Gln Met Thr Lys Glu Glu Arg Gln Ala Ala
         35                  40                  45

Gln Asn Glu Cys Gln Val Leu Lys Leu Leu Asn His Pro Asn Val Ile
     50                  55                  60

Glu Tyr Tyr Glu Asn Phe Leu Glu Asp Lys Ala Leu Met Ile Ala Met
 65                  70                  75                  80

Glu Tyr Ala Pro Gly Gly Thr Leu Ala Glu Phe Ile Gln Lys Arg Cys
                 85                  90                  95

Asn Ser Leu Leu Glu Glu Glu Thr Ile Leu His Phe Val Gln Ile
            100                 105                 110

Leu Leu Ala Leu His His Val His Thr His Leu Ile Leu His Arg Asp
        115                 120                 125

Leu Lys Thr Gln Asn Ile Leu Leu Asp Lys His Arg Met Val Val Lys
    130                 135                 140

Ile Gly Asp Phe Gly Ile Ser Lys Ile Leu Ser Ser Lys Ser Lys Ala
145                 150                 155                 160

Tyr Thr Val Val Gly Thr Pro Cys Tyr Ile Ser Pro Glu Leu Cys Glu
                165                 170                 175

Gly Lys Pro Tyr Asn Gln Lys Ser Asp Ile Trp Ala Leu Gly Cys Val
            180                 185                 190
```

-continued

```
Leu Tyr Glu Leu Ala Ser Leu Lys Arg Ala Phe Glu Ala Ala Asn Leu
            195                 200                 205

Pro Ala Leu Val Leu Lys Ile Met Ser Gly Thr Phe Ala Pro Ile Ser
210                 215                 220

Asp Arg Tyr Ser Pro Glu Leu Arg Gln Leu Val Leu Ser Leu Leu Ser
225                 230                 235                 240

Leu Glu Pro Ala Gln Arg Pro Pro Leu Ser His Ile Met Ala Gln Pro
                245                 250                 255

Leu Cys Ile Arg Ala Leu Leu Asn Leu His Thr Asp Val Gly Ser Val
                260                 265                 270

Arg Met Arg Arg Ala Glu Lys Ser Val Ala Pro Ser Asn Thr Gly Ser
            275                 280                 285

Arg Thr Thr Ser Val Arg Cys Arg Gly Ile Pro Arg Gly Pro Val Arg
            290                 295                 300

Pro Ala Ile Pro Pro Leu Ser Ser Val Tyr Ala Trp Gly Gly Gly
305                 310                 315                 320

Leu Gly Thr Pro Leu Arg Leu Pro Met Leu Asn Thr Glu Val Val Gln
                325                 330                 335

Val Ala Ala Gly Arg Thr Gln Lys Ala Gly Val Thr Arg Ser Gly Arg
                340                 345                 350

Leu Ile Leu Trp Glu Ala Pro Leu Gly Ala Gly Gly Ser Leu
            355                 360                 365

Leu Pro Gly Ala Val Glu Gln Pro Gln Pro Gln Phe Ile Ser Arg Phe
            370                 375                 380

Leu Glu Gly Gln Ser Gly Val Thr Ile Lys His Val Ala Cys Gly Asp
385                 390                 395                 400

Phe Phe Thr Ala Cys Leu Thr Asp Arg Gly Ile Ile Met Thr Phe Gly
                405                 410                 415

Ser Gly Ser Asn Gly Cys Leu Gly His Gly Ser Leu Thr Asp Ile Ser
                420                 425                 430

Gln Pro Thr Ile Val Glu Ala Leu Leu Gly Tyr Glu Met Val Gln Val
            435                 440                 445

Ala Cys Gly Ala Ser His Val Leu Ala Leu Ser Thr Glu Arg Glu Leu
450                 455                 460

Phe Ala Trp Gly Arg Gly Asp Ser Gly Arg Leu Gly Leu Gly Thr Arg
465                 470                 475                 480

Glu Ser His Ser Cys Pro Gln Gln Val Pro Met Pro Pro Gly Gln Glu
                485                 490                 495

Ala Gln Arg Val Val Cys Gly Ile Asp Ser Ser Met Ile Leu Thr Val
                500                 505                 510

Pro Gly Gln Ala Leu Ala Cys Gly Ser Asn Arg Phe Asn Lys Leu Gly
            515                 520                 525

Leu Asp His Leu Ser Leu Gly Glu Glu Pro Val Pro His Gln Gln Val
            530                 535                 540

Glu Glu Ala Leu Ser Phe Thr Leu Leu Gly Ser Ala Pro Leu Asp Gln
545                 550                 555                 560

Glu Pro Leu Leu Ser Ile Asp Leu Gly Thr Ala His Ser Ala Ala Val
                565                 570                 575

Thr Ala Ser Gly Asp Cys Tyr Thr Phe Gly Ser Asn Gln His Gly Gln
            580                 585                 590

Leu Gly Thr Asn Thr Arg Arg Gly Ser Arg Ala Pro Cys Lys Val Gln
            595                 600                 605
```

-continued

| | | | | | | | | | | | |
|---|---|---|---|---|---|---|---|---|---|---|---|
|Gly|Leu|Glu|Gly|Ile|Lys|Met|Ala|Met|Val|Ala|Cys|Gly|Asp|Ala|Phe|
| |610| | | |615| | | |620| | |

| | | | | | | | | | | | |
|---|---|---|---|---|---|---|---|---|---|---|---|
|Thr|Val|Ala|Ile|Gly|Ala|Glu|Ser|Glu|Val|Tyr|Ser|Trp|Gly|Lys|Gly|
|625| | | |630| | | |635| | | |640|

Ala Arg Gly Arg Leu Gly Arg Arg Asp Glu Asp Ala Gly Leu Pro Arg
            645                 650                 655

Pro Val Gln Leu Asp Glu Thr His Pro Tyr Thr Val Thr Ser Val Ser
        660                 665                 670

Cys Cys His Gly Asn Thr Leu Leu Ala Val Arg Ser Val Thr Asp Glu
            675                 680                 685

Pro Val Pro Pro
        690

<210> SEQ ID NO 3
<211> LENGTH: 2454
<212> TYPE: DNA
<213> ORGANISM: homo sapiens

<400> SEQUENCE: 3

| | | | | |
|---|---|---|---|---|
|atgcccgccg|ccactccagc|cccgcagccg|ccgccgcccc|cggccggcc agccccagcc|60|
|tgccggcgc|ggcctgcccc|gggacagcaa|ggcctatgtg|accattctct aaaatattta|120|
|agctcgagaa|tcacagagcg|gaagctgcaa|ggctcctggc|tgcctgccag ccagaggaat|180|
|ctggagaaac|cattcctggg|gccgcgtggc|cccgtcgtgc|ccttgttctg ccctcggaat|240|
|ggccttcact|cagcacatcc|tgagaacagc|cctctgaagc|caggttcgt gaccgtagtg|300|
|aagctgggtg|ggcagcgccc|ccgaaagatc|actctgctcc|tcaacaggcg atcagtgcag|360|
|acgttcgagc|agctcttagc|tgacatctca|gaagccttgg|gctctcccag atggaagaat|420|
|gaccgtgtga|ggaaactgtt|taacctcaag|ggcagggaaa|tcaggagcgt ctctgatttc|480|
|ttcaggaag|gggatgcttt|catagctatg|gcaaagaac|cactgacact gaagagcatt|540|
|caggtggctg|tagaagaact|gtaccccaac|aaagcccggg|ccctgacact ggcccagcac|600|
|agccgtgccc|cttctccaag|gctgaggagc|aggctgttta|gcaaggctct gaaaggagac|660|
|caccgctgtg|gggagaccga|gaccccaag|agctgcagcg|aagttgcagg atgcaaggca|720|
|gccatgaggc|accaggggaa|gatccccgag|gagctttcac|tagatgacag agcgaggacc|780|
|cagaagaagt|ggggagggg|gaaatgggag|ccagaaccca|gtagcaagcc ccagggaa|840|
|gccactctgg|aagagaggca|cgcaagggga|gagaagcatc|ttgggtgga gattgaaaag|900|
|acctcgggtg|aaattatcag|atgcgagaag|tgcaagagag|agggagct tcagcagagc|960|
|ctggagcgtg|agaggctttc|tctggggacc|agtgagctgg|atatgggaa gggcccaatg|1020|
|tatgatgtgg|agaagctggt|gaggaccaga|agctgcagga|ggtctcccga ggcaaatcct|1080|
|gcaagtgggg|aggaagggtg|gaagggtgac|agccacagga|gcagcccag gaatcccact|1140|
|caagagctga|ggagacccag|caagagcatg|gacaagaaga|aggacagagg cccagaggat|1200|
|caagaaagcc|atgctcaggg|agcagccaag|gccaagaagg|accttgtgga gttcttcct|1260|
|gtcacagagg|agggctgag|ggaggtgaag|aaggacacca|ggcccatgag caggagcaaa|1320|
|catggtggct|ggctcctgag|agagcaccag|gcgggctttg|agaagctccg caggacccga|1380|
|ggagaagaga|aggaggcaga|gaaggagaaa|agccatgta|tgtctggagg cagaaggatg|1440|
|actctcagag|atgaccaacc|tgcaaagcta|gaaaaggagc|ccaagacgag gccagaagag|1500|
|aacaagccag|agcggcccag|cggtcggaag|ccacggccca|tgggcatcat tgccgccaat|1560|
|gtggaaaagc|attatgagac|tggccgggtc|attggggatg|ggaactttgc tgtcgtgaag|1620|

-continued

```
gagtgcagac accgcgagac caggcaggcc tatgcgatga agatcattga caagtccaga    1680
ctcaagggca aggaggacat ggtggacagt gagatcttga tcatccagag cctctctcac    1740
cccaacatcg tgaaattgca tgaagtctac gaaacagaca tggaaatcta cctgatcctg    1800
gagtacgtgc agggaggaga ccttttttgac gccatcatag aaagtgtgaa gttcccggag    1860
cccgatgctg ccctcatgat catggactta tgcaaagccc tcgtccacat gcacgacaag    1920
agcattgtcc accgggacct caagccggaa aaccttttgg ttcagcgaaa tgaggacaaa    1980
tctactacct tgaaattggc tgattttgga cttgcaaagc atgtggtgag acctatattt    2040
actgtgtgtg ggaccccaac ttacgtagct cccgaaattc tttctgagaa aggttatgga    2100
ctggaggtgg acatgtgggc tgctggcgtg atcctctata tcctgctgtg tggctttccc    2160
ccattccgca gccctgagag ggaccaggac gagctcttta acatcatcca gctgggccac    2220
tttgagttcc tccccccta ctgggacaat atctctgatg ctgctaaaga tctggtgagc    2280
cggttgctgg tggtagaccc caaaaagcgc tacacagctc atcaggttct tcagcacccc    2340
tggatcgaaa cagctggcaa gaccaataca gtgaaacgac agaagcaggt gtcccccagc    2400
agcgatggtc acttccggag ccagcacaag agggttgtgg agcaggtatc atag          2454
```

<210> SEQ ID NO 4
<211> LENGTH: 817
<212> TYPE: PRT
<213> ORGANISM: homo sapiens

<400> SEQUENCE: 4

```
Met Pro Ala Ala Thr Pro Ala Pro Gln Pro Pro Pro Pro Pro Ala Arg
 1               5                   10                  15

Pro Ala Pro Ala Cys Pro Ala Arg Pro Ala Pro Gly Gln Gln Gly Leu
             20                  25                  30

Cys Asp His Ser Leu Lys Tyr Leu Ser Ser Arg Ile Thr Glu Arg Lys
         35                  40                  45

Leu Gln Gly Ser Trp Leu Pro Ala Ser Arg Gly Asn Leu Glu Lys Pro
     50                  55                  60

Phe Leu Gly Pro Arg Gly Pro Val Val Pro Leu Phe Cys Pro Arg Asn
 65                  70                  75                  80

Gly Leu His Ser Ala His Pro Glu Asn Ser Pro Leu Lys Pro Arg Val
                 85                  90                  95

Val Thr Val Val Lys Leu Gly Gly Gln Arg Pro Arg Lys Ile Thr Leu
            100                 105                 110

Leu Leu Asn Arg Arg Ser Val Gln Thr Phe Glu Gln Leu Leu Ala Asp
        115                 120                 125

Ile Ser Glu Ala Leu Gly Ser Pro Arg Trp Lys Asn Asp Arg Val Arg
    130                 135                 140

Lys Leu Phe Asn Leu Lys Gly Arg Glu Ile Arg Ser Val Ser Asp Phe
145                 150                 155                 160

Phe Arg Glu Gly Asp Ala Phe Ile Ala Met Gly Lys Glu Pro Leu Thr
                165                 170                 175

Leu Lys Ser Ile Gln Val Ala Val Glu Glu Leu Tyr Pro Asn Lys Ala
            180                 185                 190

Arg Ala Leu Thr Leu Ala Gln His Ser Arg Ala Pro Ser Pro Arg Leu
        195                 200                 205

Arg Ser Arg Leu Phe Ser Lys Ala Leu Lys Gly Asp His Arg Cys Gly
    210                 215                 220
```

-continued

```
Glu Thr Glu Thr Pro Lys Ser Cys Ser Glu Val Ala Gly Cys Lys Ala
225                 230                 235                 240

Ala Met Arg His Gln Gly Lys Ile Pro Glu Leu Ser Leu Asp Asp
            245                 250                 255

Arg Ala Arg Thr Gln Lys Lys Trp Gly Arg Gly Lys Trp Glu Pro Glu
            260                 265                 270

Pro Ser Ser Lys Pro Pro Arg Glu Ala Thr Leu Glu Glu Arg His Ala
            275                 280                 285

Arg Gly Glu Lys His Leu Gly Val Glu Ile Glu Lys Thr Ser Gly Glu
            290                 295                 300

Ile Ile Arg Cys Glu Lys Cys Lys Arg Glu Arg Glu Leu Gln Gln Ser
305                 310                 315                 320

Leu Glu Arg Glu Arg Leu Ser Leu Gly Thr Ser Glu Leu Asp Met Gly
                325                 330                 335

Lys Gly Pro Met Tyr Asp Val Glu Lys Leu Val Arg Thr Arg Ser Cys
            340                 345                 350

Arg Arg Ser Pro Glu Ala Asn Pro Ala Ser Gly Glu Glu Gly Trp Lys
            355                 360                 365

Gly Asp Ser His Arg Ser Pro Arg Asn Pro Thr Gln Glu Leu Arg
        370                 375                 380

Arg Pro Ser Lys Ser Met Asp Lys Lys Glu Asp Arg Gly Pro Glu Asp
385                 390                 395                 400

Gln Glu Ser His Ala Gln Gly Ala Ala Lys Ala Lys Lys Asp Leu Val
                405                 410                 415

Glu Val Leu Pro Val Thr Glu Gly Leu Arg Glu Val Lys Lys Asp
            420                 425                 430

Thr Arg Pro Met Ser Arg Ser Lys His Gly Gly Trp Leu Leu Arg Glu
            435                 440                 445

His Gln Ala Gly Phe Glu Lys Leu Arg Arg Thr Arg Gly Glu Glu Lys
    450                 455                 460

Glu Ala Glu Lys Glu Lys Lys Pro Cys Met Ser Gly Gly Arg Arg Met
465                 470                 475                 480

Thr Leu Arg Asp Asp Gln Pro Ala Lys Leu Glu Lys Glu Pro Lys Thr
                485                 490                 495

Arg Pro Glu Glu Asn Lys Pro Arg Pro Ser Gly Arg Lys Pro Arg
            500                 505                 510

Pro Met Gly Ile Ile Ala Ala Asn Val Glu Lys His Tyr Glu Thr Gly
            515                 520                 525

Arg Val Ile Gly Asp Gly Asn Phe Ala Val Val Lys Glu Cys Arg His
            530                 535                 540

Arg Glu Thr Arg Gln Ala Tyr Ala Met Lys Ile Ile Asp Lys Ser Arg
545                 550                 555                 560

Leu Lys Gly Lys Glu Asp Met Val Asp Ser Glu Ile Leu Ile Gln
                565                 570                 575

Ser Leu Ser His Pro Asn Ile Val Lys Leu His Glu Val Tyr Glu Thr
            580                 585                 590

Asp Met Glu Ile Tyr Leu Ile Leu Glu Tyr Val Gln Gly Gly Asp Leu
        595                 600                 605

Phe Asp Ala Ile Ile Glu Ser Val Lys Phe Pro Glu Pro Asp Ala Ala
        610                 615                 620

Leu Met Ile Met Asp Leu Cys Lys Ala Leu Val His Met His Asp Lys
625                 630                 635                 640

Ser Ile Val His Arg Asp Leu Lys Pro Glu Asn Leu Leu Val Gln Arg
```

-continued

```
                    645                 650                 655
Asn Glu Asp Lys Ser Thr Thr Leu Lys Leu Ala Asp Phe Gly Leu Ala
            660                 665                 670
Lys His Val Val Arg Pro Ile Phe Thr Val Cys Gly Thr Pro Thr Tyr
        675                 680                 685
Val Ala Pro Glu Ile Leu Ser Glu Lys Gly Tyr Gly Leu Glu Val Asp
    690                 695                 700
Met Trp Ala Ala Gly Val Ile Leu Tyr Ile Leu Leu Cys Gly Phe Pro
705                 710                 715                 720
Pro Phe Arg Ser Pro Glu Arg Asp Gln Asp Glu Leu Phe Asn Ile Ile
                725                 730                 735
Gln Leu Gly His Phe Glu Phe Leu Pro Pro Tyr Trp Asp Asn Ile Ser
            740                 745                 750
Asp Ala Ala Lys Asp Leu Val Ser Arg Leu Leu Val Val Asp Pro Lys
        755                 760                 765
Lys Arg Tyr Thr Ala His Gln Val Leu Gln His Pro Trp Ile Glu Thr
    770                 775                 780
Ala Gly Lys Thr Asn Thr Val Lys Arg Gln Lys Gln Val Ser Pro Ser
785                 790                 795                 800
Ser Asp Gly His Phe Arg Ser Gln His Lys Arg Val Val Glu Gln Val
                805                 810                 815
Ser
```

```
<210> SEQ ID NO 5
<211> LENGTH: 2824
<212> TYPE: DNA
<213> ORGANISM: homo sapiens

<400> SEQUENCE: 5
cgggctcgtg gctgctcgtc tcgcccgcc ttcccgcgcc tgctcgaccg tcgagccgcg      60
tccccgcgct gccacctctg ctccaggctc tccccgagcc cgccgccgcg ccatgcccgc     120
cgccactcca gccccgcagc cgccgccgcc ccgggcccgg ccagccccag cctgccggc     180
gcggcctgcc ccgggacagc aaggcctatg tgaccattct ctaaaatatt taagctcgag    240
aatcacagag cggaagctgc aaggctcctg gctgcctgcc agccgaggga atctggagaa    300
accattcctg gggccgcgtg gccccgtcgt gccttgttc tgccctcgga atggccttca     360
ctcagcacat cctgagaaca gccctctgaa gcccagggtc gtgaccgtag tgaagctggg    420
tgggcagcgc ccccgaaaga tcactctgct cctcaacagg cgatcagtgc agacgttcga    480
gcagctctta gctgacatct cagaagcctt gggctctccc agatggaaga atgaccgtgt    540
gaggaaactg tttaacctca agggcaggga aatcaggagc gtctctgatt tcttcaggga    600
aggggatgct ttcatagcta tgggcaaaga accactgaca ctgaagagca ttcaggtggc    660
tgtagaagaa ctgtaccca acaaagcccg ggccctgaca ctggcccagc acagccgtgc     720
ccctctcca aggctgagga gcaggctgtt tagcaaggct ctgaaaggag accaccgctg    780
tggggagacc gagaccccca agagctgcag cgaagttgca ggatgcaagg cagccatgag    840
gcaccagggg aagatccccg aggagctttc actagatgac agagcgagga cccagaagaa    900
gtggggagg gggaaatggg agccagaacc cagtagcaag cccccaggg aagccactct     960
ggaagagagg cacgcaaggg gagagaagca tcttggggtg agagattgaaa agacctcggg  1020
tgaaattatc agatgcgaga agtgcaagag agagagggga cttcagcaga gcctggagcg  1080
tgagaggctt tctctgggga ccagtgagct ggatatgggg aagggcccaa tgtatgatgt  1140
```

```
ggagaagctg gtgaggacca gaagctgcag gaggtctccc gaggcaaatc ctgcaagtgg   1200
ggaggaaggg tggaagggtg acagccacag gagcagcccc aggaatccca ctcaagagct   1260
gaggagaccc agcaagagca tggacaagaa agaggacaga ggcccagagg atcaagaaag   1320
ccatgctcag ggagcagcca aggccaagaa ggaccttgtg gaagttcttc ctgtcacaga   1380
ggaggggctg agggaggtga agaaggacac caggcccatg agcaggagca aacatggtgg   1440
ctggctcctg agagagcacc aggcgggctt tgagaagctc cgcaggaccc gaggagaaga   1500
gaaggaggca gagaaggaga aaaagccatg tatgtctgga ggcagaagga tgactctcag   1560
agatgaccaa cctgcaaagc tagaaaagga gcccaagacg aggccagaag agaacaagcc   1620
agagcggccc agcggtcgga agccacggcc catgggcatc attgccgcca atgtggaaaa   1680
gcattatgag actggccggg tcattgggga tgggaacttt gctgtcgtga aggagtgcag   1740
acaccgcgag accaggcagg cctatgcgat gaagatcatt gacaagtcca gactcaaggg   1800
caaggaggac atggtggaca gtgagatctt gatcatccag agcctctctc accccaacat   1860
cgtgaaattg catgaagtct acgaaacaga catggaaatc tacctgatcc tggagtacgt   1920
gcagggagga gacctttttg acgccatcat agaaagtgtg aagttcccgg agcccgatgc   1980
tgccctcatg atcatggact tatgcaaagc cctcgtccac atgcacgaca agagcattgt   2040
ccaccgggac ctcaagccgg aaaaccttt ggttcagcga atgaggaca aatctactac       2100 cttgaaattg gctgattttg gacttgcaaa gcatgtggtg agacctatat ttactgtgtg   2160
tgggacccca acttacgtag ctcccgaaat tctttctgag aaaggttatg gactggaggt   2220
ggacatgtgg gctgctggcg tgatcctcta tatcctgctg tgtggctttc ccccattccg   2280
cagccctgag agggaccagg acgagctctt taacatcatc cagctgggcc actttgagtt   2340 cctccccct tactgggaca atatctctga tgctgctaaa gatctggtga gccggttgct   2400
ggtggtagac cccaaaaagc gctacacagc tcatcaggtt cttcagcacc cctggatcga   2460
aacagctggc aagaccaata cagtgaaacg acagaagcag gtgtccccca gcagcgatgg   2520
tcacttccgg agccagcaca agagggttgt ggagcaggta tcatagtcac caccttggga   2580
atctgtccag cccccagttc tgctcaagga cagagaaaag gatagaagtt tgagagaaaa   2640
acaatgaaag aggcttcttc acataattgg tgaatcagag ggagagacac tgagtatatt   2700
ttaaagcata ttaaaaaaat taagtcaatg ttaaatgtca caacatattt ttagatttgt   2760
atatttaaag cctttaatac attttttgggg ggtaagcatt gtcatcagtg aggaattttg   2820
gtaa                                                                 2824
```